US009820970B2

(12) United States Patent
Nebolsin et al.

(10) Patent No.: US 9,820,970 B2
(45) Date of Patent: Nov. 21, 2017

(54) METHOD AND AGENT FOR THE TREATMENT AND PROPHYLAXIS OF DISEASES CAUSED BY (+)RNA-CONTAINING VIRUSES

(71) Applicant: OBSSCHESTVO S OGRANICHENNOI OTVETSTVENNOSTIYU "PHARMENTERPRISES", Moscow (RU)

(72) Inventors: Vladimir Evgenievich Nebolsin, Moscow (RU); Sergei Vladimirovich Borisevich, Sergiev Posad (RU); Andrei Yurievich Egorov, St. Petersburg (RU)

(73) Assignee: OBSCHESTVO S OGRANICHENNOI OTVETSTVENNOSTIYU "PHARMENTERPRISES", Moscow (RU)

( * ) Notice: Subject to any disclaimer, the term of this patent is extended or adjusted under 35 U.S.C. 154(b) by 0 days.

(21) Appl. No.: 14/424,860

(22) PCT Filed: Aug. 29, 2013

(86) PCT No.: PCT/RU2013/000751

§ 371 (c)(1),
(2) Date: Feb. 27, 2015

(87) PCT Pub. No.: WO2014/035297

PCT Pub. Date: Mar. 6, 2014

(65) Prior Publication Data

US 2015/0209330 A1 Jul. 30, 2015

(30) Foreign Application Priority Data

Aug. 30, 2012 (RU) ................................ 2012137097

(51) Int. Cl.
*A61K 31/415* (2006.01)
*A61K 31/417* (2006.01)

(52) U.S. Cl.
CPC .................................. *A61K 31/417* (2013.01)

(58) Field of Classification Search
CPC .................................................... A61K 31/417
USPC .......................................................... 514/400
See application file for complete search history.

(56) References Cited

U.S. PATENT DOCUMENTS

| | | | | |
|---|---|---|---|---|
| 6,531,452 | B1 | 3/2003 | Dragovich et al. | |
| 2003/0003075 | A1 | 1/2003 | Norio et al. | |
| 2004/0198680 | A1* | 10/2004 | Krieg | A61K 38/19 514/44 R |
| 2012/0129908 | A1 | 5/2012 | Nebolsin et al. | |

FOREIGN PATENT DOCUMENTS

| | | | |
|---|---|---|---|
| EA | 003856 | B1 | 10/2003 |
| EP | 1020179 | A2 | 7/2000 |
| EP | 1369120 | A1 | 12/2003 |
| RU | 2191594 | C1 | 10/2002 |
| WO | 9901103 | A2 | 1/1999 |
| WO | 2008036003 | A1 | 3/2008 |

OTHER PUBLICATIONS

Aring et al. "Acute Rhinosinusitis in Adults," American Family Physician, May 1, 2011, vol. 83, No. 9, pp. 1057-1063.*
Jan. 23, 2014 (WO) International Search Report—International application PCT/RU2013/000751.
J. Chen et al., Int J Infect Dis. (Oct. 2012) 16(10): e748-52.
C. C. Lin, et al., Am J Case Rep (2016) 17: 921-24.
J. D. Osguthorpe, American Family Physician (2001) 63(1): 69-76.

* cited by examiner

*Primary Examiner* — Shengjun Wang
(74) *Attorney, Agent, or Firm* — Banner & Witcoff, Ltd.

(57) ABSTRACT

The invention relates to medicine and concerns a method for the prophylaxis or treatment of diseases caused by (+)RNA-containing viruses which involves the use of an effective amount of glutaryl histamine or a pharmaceutically acceptable salt thereof. The invention also relates to a pharmaceutical composition for the prophylaxis or treatment of diseases caused by (+)RNA-containing viruses which contains an effective amount of glutaryl histamine or a pharmaceutically acceptable salt thereof. The present invention solves the problem of providing a novel agent which is effective in the treatment of diseases caused by (+)RNA-containing viruses of the *enterovirus* genus or of the *flavivirus* genus.

10 Claims, No Drawings

METHOD AND AGENT FOR THE TREATMENT AND PROPHYLAXIS OF DISEASES CAUSED BY (+)RNA-CONTAINING VIRUSES

CROSS-REFERENCE TO RELATED APPLICATIONS

This application is a U.S. National Stage application under 35 U.S.C. §371 of International Application PCT/RU2013/000751 (published as WO 2014/035297 A1), filed Aug. 29, 2013, which claims priority to Application RU 2012137097, filed Aug. 30, 2012. Benefit of the filing date of each of these prior applications is hereby claimed. Each of these prior applications is hereby incorporated by reference in its entirety.

FIELD OF THE ART

The invention relates to medicine, in particular, to use of glutaryl histamine or a pharmaceutically acceptable salt thereof for the prevention or treatment of diseases caused by (+)RNA-containing viruses.

BACKGROUND

Viral infections are a serious health problem. Today there are no developed, registered antiviral drugs against most of the hazardous and extremely dangerous viral infections, and the existing ones are often toxic to humans or insufficiently effective. Most of the existing or under-development drugs act through a specific interaction with certain viral proteins. Such drugs have a limited spectrum of action and promote fast generation of resistant viral variants. Class IV of the Baltimore virus classification system includes viruses containing single-stranded (+)RNA ((+)ssRNA). This class includes viruses belonging to the *Enterovirus* genus of the Picornaviridae family and the *Flavivirus* genus of the Flaviviridae family.

These viruses have developed an effective strategy of inhibiting the cellular antiviral programs. Such aggressive strategy of inhibiting the system of cellular antiviral protection leads to high contagiousness and pathogenicity of these groups of viruses, which is confirmed by the list of diseases caused by viruses belonging to the *Enterovirus* genus (poliomyelitis, viral rhinitis (rhinoviral cold), and *enterovirus* 71 infection) and viruses belonging to the *Flavivirus* genus (yellow fever, West Nile Fever, dengue fever, tick-borne encephalitis, St. Louis encephalitis, and Murray Valley encephalitis).

Human rhinoviruses are today the biggest problem among viruses of the *Enterovirus* genus. Rhinoviruses are the cause of upper respiratory tract diseases due to their proliferation in the nasopharyngeal mucosal cells. Rhinoviruses are causative agents of at least 80% of cold-related disease. Besides the enormous economic damage (20 million man-hours annually in the U.S.), rhinovirus infections cause a large number of complications such as sinusitis and otitis media, and are frequently detected in virological assays of children with pneumonia. In asthmatic children, rhinovirus infections are also a cause of acerbations in 80% cases. In adults, rhinoviruses can aggravate asthma as well as chronic obstructive pulmonary disease, chronic bronchitis, and mucoviscidosis, these viruses were isolated also in pneumonia-suffering patients with immunodeficiency conditions.

Since there are over 100 antigenic types of rhinoviruses, it is impossible to develop an effective vaccine (Palmenberg, A. C; Spiro, D; Kuzmickas, R; Wang, S; Djikeng, A; Rathe, J A; Fraser-Liggett, C M; Liggett, S B (2009). "Sequencing and Analyses of All Known Human rhinovirus Genomes Reveals Structure and Evolution". Science 324 (5923): 55-9. doi:10.1126/science.1165557. PMID 19213880). In addition, there is no an effective chemotherapeutic agent for the treatment of rhinovirus infection.

*Enterovirus* type 71 (EV71) was first isolated from patients with aseptic meningitis and a patient with encephalitis in California in 1970-1972. It should be noted that in severe cases the virus causes neurological disorders such as meningitis, paralysis and encephalitis. The virus is spread under unsanitary conditions. After infection with virus EV71, the temperature increases, skin rash appears on hands and feet, on the palms and soles, extremities become swollen, and ulcers appear in the oral cavity. Severe forms of *Enterovirus* may be fatal. *Enterovirus* 71 is reported to be the most "severe" among all human Enteroviruses. This virus can cause large outbreaks with fatal outcomes. Three waves of outbreaks of this infection have been recorded over the past 40 years: in 1969-1978 years in USA, Australia, Bulgaria, Japan; in 1985-1991 years in Hong Kong, Brazil, Taiwan; and in 1996-2006 years in Malaysia, Canada, China, Vietnam and Japan. For example, almost 1.5 million cases of diseases caused by *Enterovirus* 71 were recorded in Taiwan in 1998, 78 of which were fatal. In 2006-2007 years, outbreaks and individual cases of *Enterovirus* 71 occurred in India, Thailand, China, Malaysia, Brunei and Japan. There are no vaccines against *Enterovirus* 71, and non-specific therapy has not yet been developed.

Coxsackie virus infection (HCXV) is a large group of diseases characterized by pronounced clinical polymorphism. Coxsackievirus infection can be manifested by meningitis, paralysis, acute respiratory disorders, pneumonia, hemorrhagic conjunctivitis, myocarditis, hepatitis, diabetes, and other syndromes. According to the modern classification of viruses, human enteroviruses belonging to the *Enterovirus* genus are divided into 5 species (14): 1) poliovirus; 2) human *enterovirus* A; 3) human *enterovirus* B; 4) human *enterovirus* C; and 5) human *enterovirus* D. Various serotypes of Coxsackie viruses belong to the following *enterovirus* species: human *enterovirus* A (Coxsackie viruses A2-8, 10, 12, 14, and 16); human *enterovirus* B (Coxsackie viruses A9, B1-6); and human *enterovirus* C (Coxsackie viruses A1, 11, 13, 15, 17-22, and 24).

Coxsackie viruses, like other human enteroviruses, are ubiquitous in the world. In the temperate countries, their maximum circulation is in the summer-autumn season. Viruses are characterized by high invasiveness, which causes their rapid spread in the human population. Coxsackie viruses are often the cause of "sudden" outbreaks in organized children's groups and hospitals, intrafamilial spread of the infection has also been documented. A high variability of the viral genome plays an important role in the epidemiology of Coxsackie virus and other *enterovirus* infections. A consequence of this is the ability of various serotypes cause different pathology in certain circumstances. On the other hand, the same clinical syndrome may be caused by different serotypes and different *enterovirus* species. Genetic variability, selection and rapid spread of modified viruses result in major disease outbreaks, in the etiology of which these viruses have not previously been involved, or their circulation was not seen for a long time.

The primary replication of Coxsackie virus occurs in the nasopharynx- and gut-associated lymphoid tissue. It causes local lesions manifested by the symptoms of ARD, herpangina, pharyngitis, etc. In the pharynx the virus is detected until the seventh day, and excreted in the faeces for 3-4 weeks (in immunodeficiency for several years). Viraemia, in which the virus penetrates into target organs, follows the primary replication of the virus. For Coxsackie viruses the target organs include the brain and spinal cord, meninges, upper respiratory tract, lungs, heart, liver, skin, etc. Coxsackie viruses B can cause severe generalized pathological processes in newborns, resulting in necrosis in the heart, brain and spinal cord, liver and kidneys. The viruses cause the following clinic syndromes: serous meningitis (Coxsackie viruses A2, 3, 4, 6, 7, 9, 10, and B1-6); acute systemic disease in children with myocarditis and meningoencephalitis (Coxsackie viruses B1-5); paralysis (Coxsackie viruses A1, 2, 5, 7, 8, 9, 21, and B2-5); herpangina (Coxsackie viruses A2, 3, 4, 5, 6, 8, and 10); acute pharyngitis (Coxsackie viruses A10, 21); contagious rhinitis (Coxsackie viruses A21, 24); damage of the upper respiratory tract and pneumonia (Coxsackie viruses A9, 16, and B2-5) (16); pericarditis, myocarditis (Coxsackie viruses B1-5); hepatitis (Coxsackie viruses A4, 9, 20, and B5); diarrhea of newborns and infants (Coxsackie viruses A18, 20, 21, 24); acute hemorrhagic conjunctivitis (Coxsackie virus A24); foot-and-mouth-like disease (Coxsackie viruses A5, 10, 16); exanthemata (Coxsackie viruses A4, 5, 6, 9, 16); pleurodynia (Coxsackie viruses B3, 5); rash (Coxsackie virus B5); and fever (Coxsackie viruses B1-5). There are no specific chemotherapeutic agents for the treatment of Coxsackie virus infections. Pathogenic and symptomatic therapy is used depending on the clinical form of a disease.

The *Flavivirus* genus includes more than 100 viruses, ⅔ of which are arthropod-borne viruses which are pathogenic for humans. These viruses cause various diseases, from ephemeral fever to hemorrhagic fever and encephalitis.

West Nile fever (West-Nile encephalitis, Encephalitis Nili occidentalis (Lat.)) is a viral disease characterized by fever, meningitis, systemic lesion of the mucous membranes and lymph nodes. Infection is transmitted to humans through the bites of bloodsucking insects, preferably mosquitoes of the *Culex* genus (*Culex pipiens*). West Nile fever is widespread in North Africa, the Mediterranean countries, as well as in India and Indonesia. Natural foci of fever exist in Azerbaijan, Armenia, Kazakhstan, Moldova, Turkmenistan, Tajikistan, and the Astrakhan and Volgograd regions of Russia. *Flavivirus* is the genus of the viruses that are preferably transmitted by arthropods (mites and mosquitoes). Since 1999, the fever has spread throughout the United States. According to the Centers for Disease Control and Prevention (CDC), as of Aug. 21, 2012, 1118 cases of the infection were observed in 38 states, 41 people died, wherein, only in Dallas and its suburbs, 200 cases and 10 fatal cases were recorded.

Dengue fever (synonyms: breakbone fever, joint fever, giraffe fever, five-day fever, seven-day fever, date disease, dengue-awn (Ger, Fr., Isp.); dangy-fever, breakbonefever (Lat.); denguero (It.)) is a viral disease widespread in tropical and subtropical regions. Sometimes, it is encountered in temperate zones. Thus, serious outbreaks of diseases were recorded in Texas in 1922 and in Greece in 1927. The last epidemic was registered in USA in middle of 1940's. Dengue fever becomes symptomatic in 5-6 days after infection. It characterized by a sudden increase in body temperature lasting 5-7 days, headache, severe pain in muscles and joints, sometimes by rash. This is followed by a period of physical exhaustion and depression lasting for at least a week. Dengue virus pathogens are very similar to yellow fever virus and are almost universally transmitted by the same species of mosquito (mainly *Aedes aegypti*) as the yellow fever virus. Four similar dengue serotypes are identified. Infection with each of them results in a strong enough immune response, but that immunity does not particularly extend to the other serotypes. Two extremely severe forms of the disease—dengue hemorrhagic fever and dengue shock syndrome—were registered in Southeast Asia during the 1950s. In young children they caused prostration and death, wherein the number of fatal cases was too large. The reasons for such severe progression of the disease remain unclear. Mutations of some strains of dengue virus seem to result in generation of more pathogenic forms. It is possible that reinfection with other virus serotypes has taken place over a short time period, thereby leading to the disruption in immune mechanisms. There are no specific agents for the treatment of dengue fever. Corticosteroids and antibiotics are used in hemorrhagic fever and shock syndrome, but their effectiveness is not proven. In case of shock syndrome it is recommended to maintain the water balance of the body and to administer plasma-volume expanding agents. Vaccines against dengue fever are still being developed, but without definite results. Moreover, if the suggestion that the development of severe hemorrhagic and shock syndromes is caused by sensitization (increase in sensitivity) of the immune system is proved, the appropriateness of immune vaccination will be questioned.

Tick-borne encephalitis (spring-summer, vernal, Russian, woodcutter encephalitis, Encephalitis ocarina (Lat.)) is natural focal transmissible (mite-transmitted) viral infection characterized by predominant damage of the central nervous system. The incubation period of the disease lasts from 7 to 14 days and may be longer. The disease usually begins with a fever and myalgia lasting from 2 to 4 days. This period is suggested to correspond to viraemia. Then, after a short remission period lasting for a few days, the second wave of fever comes and meningeal symptoms appear. The spectrum of clinical manifestations of this stage of the disease is quite broad—from serous meningitis specific to relatively young people to the severest forms of encephalitis with coma, epilepsy, tremor and movement disorders, lasting 7-10 days. Lesions in the spinal cord and medulla oblongata cause a risk of paralysis of the respiratory muscles and the shoulder girdle muscles. Most patients recover, but sometimes there remain severe neurological defects. Etiotropic treatment of this infection does not exist. Effective inactivated vaccines against tick-borne encephalitis are produced with aluminum salts as an adjuvant. Tick-borne encephalitis vaccine produced in Austria provides antiviral immunity when administered twice within from 0.5 to 3 months. The rest of vaccines are at lest similarly effective. In rare cases, vaccination is complicated by Guillain-Barre syndrome, for this reason it is recommended only for people living within the natural foci or visiting them in the spring and summer. In the natural foci, infected ticks are from 0.2 to 4.0%, so, if a tick is discovered attached to a person, acute immunization becomes actual. Immunoglobulin against tick-borne encephalitis can be administered immediately; however, many people have contraindications to it due to allergic reactions.

Saint-Louis encephalitis (Encephalitis Americana (Lat.)) is endemic in most regions in the USA, Mexico, Argentina, Suriname, the Caribbean, Colombia, and southern Canada. During an outbreak, the disease affects from hundreds to thousands of people with 15-30% mortality. In North America, natural foci are maintained by wild birds and mosquitoes of the *Culex* genus. The disease appears suddenly and is accompanied by fever, nausea, vomiting, headache, and meningeal syndrome, followed by ataxia, speech impairment, urinary incontinence, confusion, and tremor. Its progression may be fulminant. Residual changes in the CNS develop in 5% cases. A specific treatment and prevention of the disease has not been developed up to the present time. Attempts to develop a vaccine have failed. Thus, the use of a formulated vaccine made from infected mouse brains provides only short-term immunity in vaccinated people. Only pathogenic and symptomatic agents are used.

Murray Valley encephalitis (Encephalitis Avstralia (Lat.)) is endemic in Australia, New Zealand and the surrounding area. During seasonal outbreaks, mortality reaches 20-50%. In Australia, natural foci are maintained by wild birds (herons) and mosquitoes of the *Culex* genus. The disease is accompanied by fever, headache, meningeal syndrome, and often paralysis. A specific treatment and prevention of the disease has not been developed up to the present time. Only pathogenic and symptomatic agents are used.

It should be noted that the only chemotherapeutic agent exerting some beneficial effects in infections caused by (+)RNA-containing viruses is ribavirin. However, ribavirin is relatively toxic drug, often causing anemia. Its main feature is a long-term storage in erythrocytes. As a result, traces of ribavirin are detected even 6 months after the end of therapy. There are references to the teratogenicity of ribavirin.

DESCRIPTION OF THE INVENTION

The inventors have unexpectedly found that glutaryl histamine can be used as a non-toxic antiviral agent against infections caused by viruses belonging to, but not limited to, the *Enterovirus* and *Flavivirus* genera.

In view of the above, the present invention relates to an agent for the treatment and/or prevention of diseases caused by (+)RNA-containing viruses belonging to the *Enterovirus* genus or the *Flavivirus* genus, wherein the agent is glutaryl histamine of the following formula:

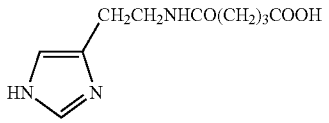

Glutaryl histamine according to the invention is administered in a solid dosage form.

The invention also relates to a method for the prevention and treatment of diseases caused by (+)RNA-containing viruses belonging to the *Enterovirus* genus or the *Flavivirus* genus, the method comprising administering an effective amount of glutaryl histamine or a pharmaceutically acceptable salt thereof to a patient.

The virus belonging to the *Enterovirus* genus can be selected from the group including rhinoviruses, Coxsackie viruses and *enterovirus* type 71. The virus belonging to the *Flavivirus* genus can be selected from the group including West Nile virus, dengue virus, tick-borne encephalitis virus, Saint-Louis encephalitis virus, Murray Valley encephalitis virus, and yellow fever virus. A dose of glutaryl histamine or a pharmaceutically acceptable salt thereof can be from 0.1 to 30 mg/kg of patient's body weight. A single dose of glutaryl histamine can be about 100 mg. A preferable duration of the administration of glutaryl histamine can be from 5 days to 12 months. One embodiment of the invention relates to the prevention or treatment of aggravations of asthma, chronic obstructive pulmonary disease, bronchitis and mucoviscidosis, which are caused by rhinoviruses.

Further, the invention relates to a pharmaceutical composition for the treatment of diseases caused by (+)RNA-containing viruses belonging to the *Enterovirus* genus or the *Flavivirus* genus, wherein the composition comprises an effective amount of glutaryl histamine or a pharmaceutically acceptable salt thereof. The effective amount of glutaryl histamine or a pharmaceutically acceptable salt thereof is preferably from 0.1 to 30 mg/kg of patient's body weight. A dose of glutaryl histamine can be 100 mg in once-daily administration.

The invention also relates to a kit for the treatment of diseases caused by (+)RNA-containing viruses belonging to the *Enterovirus* genus or the *Flavivirus* genus, wherein the kit includes the composition according to the invention and instructions for use thereof.

In addition, the invention relates to use of glutaryl histamine or a pharmaceutically acceptable salt thereof for preparing a pharmaceutical composition for the treatment of diseases caused by (+)RNA-containing viruses belonging to the *Enterovirus* genus or the *Flavivirus* genus. The invention also relates to use of glutaryl histamine or a pharmaceutically acceptable salt thereof for the treatment of diseases caused by (+)RNA-containing viruses belonging to the *Enterovirus* genus or the *Flavivirus* genus.

Pharmaceutically acceptable salts of glutaryl histamine according to the invention can be alkali or alkaline-earth metals salts thereof, preferably sodium, potassium, and lithium salts.

Glutaryl histamine or salts thereof are administered in an effective amount to provide a desired therapeutic result.

Glutaryl histamine or salts thereof can be administered to a patient in a dose of from 0.1 to 30 mg/kg of human body weight, preferably in a dose of from 0.3 to 1.5 mg/kg, one or more times a day.

It should be noted that a particular dose for each particular patient depends on many factors, such as patient's age, body weight, gender, general health condition, and diet; the schedule and route of the administration of the agent and its excretion rate from the body; and disease severity in treated patients.

The pharmaceutical compositions according to the invention comprise glutaryl histamine or a pharmaceutically acceptable salt thereof in an amount effective to provide a desired result, and can be prepared in unit dosage forms (for example, in solid, semi-solid, or liquid forms) which comprise glutaryl histamine or a salt thereof as an active agent in a mixture with a carrier or an excipient suitable for intramuscular, intravenous, oral, sublingual, inhalation, intranasal, rectal, and transdermal administration. The active agent can be added to the composition together with conventional nontoxic pharmaceutically acceptable carriers suitable for the manufacture of solutions, tablets, pills, capsules, pellets, suppositories, emulsions, suspensions, ointments, gels, patches, and any other dosage forms.

Various compounds can be used as excipients, such as saccharides, for example, glucose, lactose or sucrose; mannitol or sorbitol; cellulose derivatives; and/or calcium phosphates, for example, tricalcium phosphate or calcium hydrophosphate. The following compounds can be used as a binder: starch paste, for example, corn, wheat, rice, or potato starch, gelatin, tragacanth, methylcellulose, hydroxypropylmethylcellulose, sodium carboxymethylcellulose, and/or polyvinylpyrrolidone. Disintegrating agents can be optionally used, such as the aforementioned starches and carboxymethyl starch, cross-linked polyvinylpyrrolidone, agar-agar, or alginic acid or a salt thereof, such as sodium alginate.

Optional additives, such as flow control agents and lubricating agents, for example, silica, talc, stearic acid and salts thereof, for example, magnesium stearate or calcium stearate, and/or propylene glycol, are also can be used.

Stabilizing agents, thickening agents, colorants, and flavoring agents also can be used as additives.

An ointment base can be selected from hydrocarbon ointment bases, such as white Vaseline and yellow Vaseline (*Vaselinum album* and *Vaselinum flavum*, respectively), Vaseline oil (*Oleum Vaselini*), and white ointment and liquid ointment (*Unguentum album* and *Unguentum flavum*, respectively), wherein solid paraffin and wax can be used as a thickening additive. Absorptive ointment bases, such as hydrophilic Vaseline (*Vaselinum hydrophylicum*), lanoline (*Lanolinum*), and cold cream (*Unguentum leniens*); water-removable ointment bases, such as hydrophilic ointment (*Unguentum hydrophylum*); and water-soluble ointment bases, such as polyethylene glycol ointment (*Unguentum Glycolis Polyaethyleni*); bentonite bases; and others are also suitable.

Methylcellulose, sodium carboxymethylcellulose, oxypropylcellulose, polyethylene glycol or polyethylene oxide, and carbopol are useful as a base for gels.

Water-insoluble bases such as cocoa butter; water-soluble or water-miscible bases, such as gelatin-glycerol or polyethylene oxide bases; and combination (soap-glycerol) bases are useful as a base for suppositories.

In a unit dosage form, the amount of an active agent used in combination with a carrier can vary depending on a patient to be treated and a particular route of administration of a therapeutic agent.

For example, when glutaryl histamine or a salt thereof is used in the form of a solution for injections, the active agent in the solution is in an amount of 0.1 to 5%. Suitable diluents are 0.9% sodium chloride solution, distilled water, Novocain solution for injections, Ringer solution, glucose solution, and specific solubilizing additives. When glutaryl histamine or a salt thereof is administered in the form of tablets or suppositories, its amount ranges 10 to 300 mg per unit dosage form.

Dosage forms according to the invention are produced by standard methods, such as blending, granulation, forming pellets, dissolution, and lyophylization.

It should be noted that no adverse side effects have been registered during long-term administration of glutaryl histamine or a salt thereof in therapeutic doses or doses which are greater by an order of magnitude than therapeutic ones.

EMBODIMENT OF THE INVENTION

The following examples disclose the invention in more details to demonstrate the effectiveness of glutaryl histamine for the prevention and treatment of diseases according to the present invention, where the disclosed examples are not intended to limit the scope of the invention.

Example 1

Antiviral Activity of Glutaryl Histamine Against a Human Rhinovirus on an In Vivo Experimental Model The study was performed with a human rhinovirus strain (HRV 1B) preliminarily adapted to the proliferation in the mouse lungs.

Specificity of HRV was controlled by a polymerase chain reaction (PCR), Real-time PCR (AmpliSense, Russia) and two-round PCR with primers specific for RNA derived from the suspension of lungs and trachea of HRV-infected mice by using “Ribo-sorb” kit manufactured by “AmpliSense”.

White Balb/c male mice weighed from 8 to 10 g were infected with virus-containing material in an amount of 0.05 ml/mouse intranasally under brief ether anesthesia.

The mice were handled according to the Guidelines for the Care and Use of Laboratory Animals. Before the study, the animals were quarantined for five days.

The animals were provided with standard food ration and kept under the same conditions. Mice were divided into groups of 10 animals each.

Glutaryl histamine was administered orally once daily for 3 days, starting at 12 hours after infection of the mice with HRV. Mice of the control group were administered normal saline under the same conditions.

Glutaryl histamine was administered in doses 15 and 30 mg/kg.

HRV infection titers in suspensions of mouse trachea and lungs 48 and 72 hours after infection were determined by individual analysis of 10% suspension derived from each mouse in a series of 10-fold dilutions on cell culture Hela. Results were assessed by PCR at 2 hours after incubation at 33° C.

Each dilution of a test probe was assessed in four wells of a plate, and the obtained values were used to calculate a mean value. The maximum dilution of infected culture supernatant wherein the viral RNA was detected by PCR was accepted as a virus titer. The titer was expressed as the reciprocal value of the virus dilution in which HRV RNA was determined (lg/ml is represented as a mean value: lg±m).

Statistic analysis of the results was performed using Microsoft Excel software.

The effectiveness of glutaryl histamine was evaluated by the suppression of the virus reproduction in lungs at 48 and 72 hours after HRV infection.

Criteria of the in vivo glutaryl histamine effectiveness were a reduction in the accumulation of virus in lungs, determined based on infectious titer in the cell culture Hela and directly in suspensions of mouse lungs by a PCR method.

Results of the determination of the infectious activity of HVR in suspensions of mouse lungs in the cell culture Hela are given in Table 1.

Titration of lung suspensions of the HVR infected mice showed proliferation of the virus in the lungs, which reached the maximum value of 4.1 lg in 48 hours, and 3.2 lg in 72 hours in the control group. The use of glutaryl histamine led to a quite pronounced reduction in the infectious activity of HRV, in particular by 2.6 and 2.2 lg, respectively, in a used dose of glutaryl histamine of 30 mg/kg.

The same results were obtained in studying the effectiveness of glutaryl histamine against HVR infection in mice by the suppression and activity of the virus directly in lungs by a PCR method. Real time PCR demonstrated a significant reduction in the amount of viral RNA copies at 48 and 72 hours after infection, namely from 10 to 100 times, in the group of mice administered glutaryl histamine, compared to the control groups.

Thus, this example shows a possibility of using glutaryl histamine as an effective antiviral agent which specifically decreases the reproduction of the human rhinovirus.

TABLE 1

Infectious titer of the HVR virus in the mouse lungs in 48 and 72 hours

| Drug | Total amount of animals in each group (n) | Infectious virus titer in lungs, lg, $TCID_{50}$ | Suppression of the virus reproduction (Δ lg) | P |
|---|---|---|---|---|
| Glutaryl histamine, 15 mg/ml (48 hrs) | 10 | 2.8 ± 0.4 | 1.3 | 0.01 |
| Glutaryl histamine, 30 mg/ml (48 hrs) | 10 | 1.5 ± 0.3 | 2.6 | 0.001 |
| Normal saline (48 hrs) | | 4.1 ± 0.4 | | |
| Glutaryl histamine, 15 mg/ml (72 hrs) | 10 | 2.1 ± 0.3 | 1.1 | |
| Glutaryl histamine, 30 mg/ml (72 hrs) | 10 | 1.0 ± 0.3 | 2.2 | 0.01 |
| Normal saline (72 hrs) | 10 | 3.2 ± 0.4 | | |

Example 2

Study of the Effectiveness of Glutaryl Histamine Against an Experimental Form of West Nile Fever (WNF)

In the experiment West Nile virus strain Eg101 was used. Infected animals were monitored for 21 days. Their death was controlled, and the average lifetime of the white mice were calculated in the experimental and control groups.

The main criteria of the in vivo effectiveness were the values of protection of the laboratory animals against death and the average lifetime of the animals in a group.

To estimate the effectiveness of glutaryl histamine, white mice were infected subcutaneously with a dose of $10LD_{50}$. Glutaryl histamine was administered orally according to the following schemes: for prevention—in a dose of 5 mg/kg, once daily for 4 days before infection and at 1 hour before infection; in a dose of 30 mg/kg, once weekly; for treatment—in a dose of 5 mg/kg, at 24 after infection and then for 7 days; in a dose of 30 mg/kg, once daily at 24 and 48 hours after infection, then a single dose of 15 mg/kg in 72, 96 and 120 hours.

Results of the evaluation of the effectiveness given in Table 2 demonstrate that glutaryl histamine protects infected mice against death when administered in a dose of 5 mg/kg by the prevention and treatment schemes. The protection against death was 42.9% and 37.8%, respectively. In addition, the average lifetime of the animals in the groups significantly increased (by 4.2 and 2.8 days, respectively).

TABLE 2

Results of the study of the glutaryl histamine effectiveness on the experimental model of West Nile Fever in white mice

| Drug | Scheme | Protective ratio, % | Average lifetime, days | Extension of the average lifetime, Δ, days |
|---|---|---|---|---|
| Glutaryl histamine | −96 h, −72 h, −48 h, −24 h, −1 h | 42.9 | 11.2 | 4.2 |
| | +24 h, +48 h, +72 h, +96 h, +120 h, +144 h, +168 h | 37.8 | 9.8 | 2.8 |
| Control of a virus dose (without drug) | | — | 7.0 | — |
| Control of a herd | | — | 21.0 | — |

In the second therapeutic scheme (Table 3), the protective effectiveness of glutaryl histamine in a dose of 30 mg/kg on the experimental model of West Nile Fever in white mice in a single administration at 144 hours before infection was 40.0% and an increase in the average lifetime of the animals was 3.7 days.

TABLE 3

Results of the study of the glutaryl histamine effectiveness on the experimental model of West Nile Fever in white mice in a single administration before infection

| Drug | Drug dose, mg/kg | Drug administration scheme | Protection against death, % | Average lifetime of animals in a group, days | Extension of the average lifetime of animals in a group, Δ, days |
|---|---|---|---|---|---|
| Glutaryl histamine | 30 | −144 h | 40.0 | 10.8 | 3.7 |
| Control of a virus dose (without drug) | | | — | 7.1 | — |
| Control of a herd | | | | 21.0 | |

Results of the evaluation of the effectiveness given in Table 4 demonstrate that the agent effectively protects the infected mice against death in administration thereof by the treatment scheme (30 mg/kg once daily for 2 days, then 15 mg/kg once daily for 3 days). The protection against death was 50.0% and the average lifetime of the animals in the group increased by 3.5 days. The reference medicament ribavirin protected against death 50% of animals when administered by the prevention scheme in a dose of 20 mg/kg. It should be noted that the protective effectiveness of ribavirin in the administration thereof by the treatment scheme was 10.0%.

Thus, in the experimental form of West Nile Fever (WNF), glutaryl histamine effectively protected the infected animals against death.

TABLE 4

Results of the glutaryl histamine effectiveness in the
experimental form of West Nile Fever in white mice

| Drug | Drug dose, mg/kg | Drug administration scheme | Protection against death, % | Average lifetime of animals in a group, days | Extension of the average lifetime of animals in a group, Δ, days |
|---|---|---|---|---|---|
| Glutaryl histamine | 30/15 | +24 h, +48 h, +72 h, +96 h, +120 h | 50.0 | 11.5 | 4.5 |
| Ribavirin | 20 | | 10.0 | 7.2 | 0.2 |
| Control virus dose (without drug) | | | — | 7.0 | — |
| Control of a herd | | | | 21.0 | |

Example 3

Study of the Glutaryl Histamine Effectiveness on an Experimental Model of a Tick-Borne Encephalitis Virus (TBE)

The glutaryl histamine effectiveness was studied on the experimental model of TBE in white mice weighed from 9 to 10 g which were infected subcutaneously with TBE virus strain Sof' in in a dose of $30LD_{50}$. Glutaryl histamine was administered orally in a dose of 5 mg/kg by the prevention scheme (at 5 days before infection, once daily); by the prevention/treatment scheme (at 5 days before infection and for 7 days after infection, once daily); by the treatment scheme (at 24 hours after infection and then for 7 days, once daily); as well as in a dose of 30 mg/ml, by the prevention scheme (once a week); by the treatment scheme (once daily at 24 and 48 hours after infection, then in a single dose of 15 mg/kg in 72, 96 and 120 hours).

Ribavirin was used as a reference medicament by the emergency prevention scheme in a dose of 20 mg/kg.

Results of the studies given in Table 5 demonstrate that the maximum antiviral effectiveness of glutaryl histamine was observed when glutaryl histamine was administered by the prevention and prevention/treatment schemes. It was showed that protection against death was 40% and an increase in the average lifetime was 4.2 days. In the administration by the prevention and prevention/treatment schemes, the protective effectiveness of glutaryl histamine was 35%.

TABLE 5

Results of the study of the glutaryl histamine effectiveness
on the experimental model of TBE in white mice

| Drug | Drug administration scheme | Average lifetime, days | Extension of the average lifetime, Δ, days | Protective ratio, % |
|---|---|---|---|---|
| Glutaryl histamine | −96 h, −72 h, −48 h, −24 h, −1 h | 15.1 | 3.9 | 35.0 |
| | −120 h, −96 h, −72 h, −48 h, −24 h, +1 h, +24 h, +48 h, +72 h, +96 h, +120 h, +144 h | 15.4 | 4.2 | 40.0 |
| | +1 h, +24 h, +48 h, +72 h, +96 h, +120 h, +144 h | 13.6 | 2.4 | 35.0 |
| Ribavirin | +1 h, +24 h, +48 h, +72 h, +96 h, +120 h, +144 h | 15.0 | 3.8 | 35.0 |

TABLE 5-continued

Results of the study of the glutaryl histamine effectiveness
on the experimental model of TBE in white mice

| Drug | Drug administration scheme | Average lifetime, days | Extension of the average lifetime, Δ, days | Protective ratio, % |
|---|---|---|---|---|
| Control of a virus dose (without drug) | | 11.2 | | |
| Control of a herd | | 21.0 | — | — |

"−"—the administration of a medicament before infection;
"+"—the administration of a medicament after infection.

In the second prevention scheme (Table 6), the protective effectiveness of glutaryl histamine in a dose of 30 mg/kg on the experimental model of tick-borne encephalitis in white mice in a single administration at 144 hours before infection was 30.0% and an increase in the average lifetime of the animals was 3.1 days.

TABLE 6

Results of the evaluation of the glutaryl histamine
effectiveness on the experimental model of tick-borne
encephalitis in white mice in a single administration in a
dose of 30 mg/kg before infection

| Drug | Drug administration scheme | Average lifetime, days | Extension of the average lifetime, days | Protection against death, % |
|---|---|---|---|---|
| Glutaryl histamine | −144 h | 10.5 | 3.1 | 30.0 |
| Control of a virus dose (without drug) | | 7.4 | | |
| Control of a herd | | 21.0 | | |

Results of the evaluation of the effectiveness given in Table 7 demonstrate that the glutaryl histamine effectively protects the infected mice against death in administration thereof by the treatment scheme (30 mg/kg once daily for 2 days, then 15 mg/kg once daily for 3 days). Protection against death was 40.0% and the average lifetime of the animals in the group increased by 3.2 days. It should be noted that the protective effectiveness of ribavirin when administered by the treatment scheme was 15.0%.

Thus, in the experimental model of tick-borne encephalitis, glutaryl histamine effectively protects the infected animals against death.

TABLE 7

Results of the evaluation of the glutaryl histamine
effectiveness on the experimental model of tick-borne
encephalitis in white mice administered with a dose of 30/15
mg/kg

| Drug | Drug administration scheme | Average lifetime, days | Extension of the average lifetime, days | Protection against death, % |
|---|---|---|---|---|
| Glutaryl histamine | +24 h, +48 h, +72 h, +96 h, | 10.1 | 3.2 | 40.0 |

TABLE 7-continued

Results of the evaluation of the glutaryl histamine effectiveness on the experimental model of tick-borne encephalitis in white mice administered with a dose of 30/15 mg/kg

| Drug | Drug administration scheme | Average lifetime, days | Extension of the average lifetime, days | Protection against death, % |
|---|---|---|---|---|
| Ribavirin | +120 h | 7.2 | 0.3 | 15.0 |
| Control of a virus dose (without drug) | | 6.9 | | |
| Control of a herd | | 21.0 | | |

Example 4

Study of the Effectiveness of Glutaryl Histamine in Experimental Form of Dengue Fever To determine antiviral activity, white mice were infected intracerebrally with a dengue fever virus. Glutaryl histamine was administered orally by the following schemes: for prevention—in a dose of 5 mg/kg, once daily for 4 days before infection and at 1 hour before infection; in a dose of 30 mg/kg, once weekly; for treatment—in a dose of 5 mg/kg, at 24 after infection and then for 7 days; in a dose of 30 mg/kg, once daily in 24 and 48 hours, then in a dose of 15 mg/kg once daily at 72, and 120 hours after infection. Infected animals were monitored for 21 days. Biological samples were evaluated on day 5 after infection.

Results of the effectiveness evaluation given in Table 8 demonstrate that glutaryl histamine inhibits effectively the proliferation of the dengue hemorrhagic fever virus in the mice blood when administered by the prevention and treatment schemes in a dose of 5 mg/kg. The level of inhibition of the virus accumulation was 95.5%.

TABLE 8

Results of the study of the effectiveness of inhibition of the dengue fever virus proliferation in the blood of white mice infected intracerebrally with a dose of 5 mg/kg, obtained on the experimental form of dengue fever

| Drug | Scheme | Level of virus accumulation in the blood, lg PFU/ml | Reduction in the level of virus accumulation, lg | Degree of inhibition of the virus accumulation, % |
|---|---|---|---|---|
| Glutaryl histamine | −96 h, −72 h, −48 h, −24 h, −1 h | 5.0 | 1.6 | 95.5 |
| | +24 h, +48 h, +72 h, +96 h, +120 h, +144 h, +168 h | 4.8 | 1.8 | 98.6 |
| Control of a virus dose (without drug) | | 6.6 | | |

Results of the evaluation of the effectiveness given in Table 9 demonstrate that glutaryl histamine effectively inhibits the proliferation of the dengue hemorrhagic fever virus in the blood of white mice when administered by the treatment scheme (30 mg/kg once daily for 2 days, then 15 mg/kg once daily for 3 days). The level of inhibition of the virus accumulation was 99.6%. It should be noted that in the treatment scheme the level of inhibition of the virus accumulation in the blood of the animals treated with ribavirin was only 83.4%.

Thus, in case of dengue hemorrhagic fever, glutaryl histamine effectively inhibits the virus replication in infected animals.

TABLE 9

Results of the study of the effectiveness of inhibition of the dengue hemorrhagic fever virus proliferation in the blood of white mice infected intracerebrally with a dose of 30/15 mg/kg, obtain on the experimental form of dengue hemorrhagic fever

| Drug | Scheme | Level of virus accumulation in the blood, lg PFU/ml | Reduction in the level of virus accumulation, lg | Degree of inhibition of the virus accumulation, % |
|---|---|---|---|---|
| Glutaryl histamine | +24 h, +48 h, +72 h, +96 h, | 4.8 | 2.6 | 99.6 |
| Ribavirin | +120 h | 6.4 | 1.0 | 83.4 |
| Control of a virus dose (without drug) | | 7.4 | | |

Example 5

Antiviral Effect of Glutaryl Histamine Against a Coxsackie Virus

In the study, a trypsin-dependent strain HCXV was used that was previously adapted and caused death of Coxsackie virus-infected mice.

The experiment was carried out on white mice weighed 6 to 7 g.

The animals were infected intramuscularly in a dose of 0.1 ml/mouse. The dose used in the experiment was $10LD_{50}$ which caused 70-80% lethality in mice.

The therapeutic capability of glutaryl histamine was evaluated by a mortality rate in the HCXV virus-infected mice in the test group compared with the group of untreated mice.

The test drugs and placebo were administered orally by the treatment scheme. Normal saline solution was administered to mice as placebo. 14 intact animals that were kept in a separate room under the same conditions as the experimental animals were used as a negative control.

The experiment was conducted on 4 groups by 14 animals. The animals of the first, second and the third groups were administered glutaryl histamine in a dose of 30 mg/kg, 3 mg/kg, and 0.3 mg/kg of body weight, respectively, and the animals of the fourth control group were received a normal saline solution. The drugs were administered orally once daily for 5 days (first administration—at 24 hours after the infection). The animals were monitored for 20 days, during which the animals were weighed every day, and the mortality rate was registered.

During the study the glutaryl histamine effectiveness in HCXV virus-infected animals, none of non-specific fatal cases were registered in the control group of intact animals.

TABLE 10

| Protective effectiveness of glutaryl histamine against an HCXV virus | | | | | |
|---|---|---|---|---|---|
| Dose of glutaryl histamine | Total number of animals in a group (n) | Total mortality rate | Average lifetime, (%) | Extension of the days lifetime, Δ, days | Protective ratio, % average |
| 30 mg/kg | 14 | 57.1 | 19.6 | +9.6 | 27.4 |
| 3 mg/kg | 14 | 50.0 | 21.7 | +11.7 | 36.4 |
| 0.3 mg/kg | 14 | 42.9 | 24.4 | +14.4 | 45.4 |
| Virus | 14 | 78.6 | 10.0 | | |

Results of the study demonstrate that first fatal cases in the group of virus-infected mice, which were not administered glutaryl histamine, were registered on day 7 after the infection, and 78.6% of the mice died up to day 9. The average lifetime in the control group was 10.0 days.

Glutaryl histamine demonstrate a statistically significant protective effect against the experimental model of infection with the Coxsackie virus, expressed in a decrease of the mortality rate among the animals and in an increase in the average lifetime of the animals.

A high antiviral activity of glutaryl histamine described in this example evidences that this agent is useful as an effective drug in the treatment of HCXV *enterovirus* infections.

Example 6

The Manufacture of Dosage Forms of Glutaryl Histamine

Dosage forms of glutaryl histamine used according to the present invention are prepared by standard methods such as, for example, processes of mixing, granulating, forming pills, dissolving and lyophilizing.

Tableted Form

A tableted form is prepared by using the following ingredients:

| | |
|---|---|
| Glutaryl histamine or a pharmaceutically acceptable salt thereof | from 1 to 100 mg |
| Potato starch | from 20 to 50 mg |
| Magnesium stearate | from 3 mg |
| Aerosil | 1 mg |
| Lactose | up to 300 mg |

The ingredients are mixed and compressed to form tablets weighing 300 mg

| Gelatinous capsules | |
|---|---|
| Glutaryl histamine or a pharmaceutically acceptable salt thereof | 90 mg |
| Lactose (milk sugar), potato starch, colloidal silica (Aerosil), magnesium stearate | up to 220 mg in capsule |

The above-mentioned ingredients are mixed and granulated, and the resulting granules are placed into solid gelatinous capsules in an amount of 220 mg.

| Suppositories<br>Example of the formulation of a suppository | |
|---|---|
| Glutaryl histamine or a pharmaceutically acceptable salt thereof | from 1 to 100 mg |
| Cacao oil | in an amount required for a suppository |

Rectal, vaginal, and urethral suppositories can be optionally prepared by using corresponding excipients.

Solution for Injections

Example 1 of the formulation of a solution for injections:

| | |
|---|---|
| Glutaryl histamine or a pharmaceutically acceptable salt thereof | from 1 to 100 mg |
| Water for injections | 2 ml |

A solution for injections can be prepared by using 0.9% sodium chloride solution, distilled water and a Novocain solution, as a diluent. Pharmaceutical forms include ampules, flasks, syringe-tubes, and "inserts".

Formulation 1 of a solution for injections:

| | |
|---|---|
| Glutaryl histamine or a salt thereof | 100 mg |
| Distilled water | 5 ml |

A solution for injections can be prepared by using 0.9% sodium chloride solution, isotonic phosphate buffer, or HEPES, as a diluent. Pharmaceutical forms include ampules, flasks, syringe-tubes, and "inserts".

Formulations for injections can be prepared in various dosage units such as sterile solution, sterile powders, and tablets.

The invention claimed is:

1. A method for treating a disease caused by a (+)RNA-containing virus, the method comprising administering an effective amount of glutaryl histamine or a pharmaceutically acceptable salt thereof to a patient, wherein the (+)RNA-containing virus is selected from the group consisting of a rhinovirus, a coxsackie virus, a West Nile virus, a dengue fever virus, and a tick-borne encephalitis virus.

2. The method of claim 1, wherein the disease is an aggravation of asthma, chronic obstructive pulmonary disease, bronchitis, or mucoviscidosis, which is caused by a rhinovirus.

3. The method of claim 1, wherein the glutaryl histamine is administered in a solid dosage form.

4. The method of claim 1, wherein the glutaryl histamine or pharmaceutically acceptable salt thereof is administered in a total dosage amount of from 0.1 to 30 mg/kg of body weight of the patient.

5. The method of claim 1, wherein a daily dose of glutaryl histamine is 100 mg.

6. The method of claim 1, wherein duration of the glutaryl histamine administration is from 5 days to 12 months.

7. The method of claim 4, wherein the total dosage amount from 0.1 to 10 mg/kg of body weight of the patient.

8. The method of claim 1, wherein the glutaryl histamine or pharmaceutically acceptable salt thereof is administered in a dose of from 0.3 to 1.5 mg/kg of body weight of the patient, one or more times a day.

9. The method of claim 1, wherein the pharmaceutically acceptable salt is an alkali or alkaline-earth metal salt.

10. The method of claim 9, wherein the alkali or alkaline-earth metal salt is selected from the group consisting of a sodium salt, a potassium salt, and a lithium salt.

* * * * *